United States Patent [19]
Santiesteban et al.

[11] Patent Number: 6,147,185
[45] Date of Patent: Nov. 14, 2000

[54] 1,4-DIAZABICYCLO[2.2.2]OCTANE COMPOUNDS AND THEIR USE FOR THE PRODUCTION OF POLYURETHANES

[75] Inventors: José Guadalupe Santiesteban, West Chester; Roy Daniel Bastian, Bethlehem; John Nelson Armor, Orefield; Mark Leo Listemann, Kutztown; Lisa Ann Mercando, Pennsburg, all of Pa.

[73] Assignee: Air Products and Chemicals, Inc., Allentown, Pa.

[21] Appl. No.: 09/359,755

[22] Filed: Jul. 23, 1999

[51] Int. Cl.[7] .................. C08G 73/06; C07D 241/36
[52] U.S. Cl. .................. 528/423; 528/423; 544/342; 544/343
[58] Field of Search .................. 528/423; 544/342, 544/343; 514/250; 264/331.19; 428/160

[56] References Cited

U.S. PATENT DOCUMENTS

| | | | |
|---|---|---|---|
| 3,297,701 | 1/1967 | Brader et al. ................ | 260/268 |
| 3,375,252 | 3/1968 | Yamada et al. ............... | 260/268 |
| 4,804,758 | 2/1989 | Hoelderich et al. .......... | 544/352 |
| 5,041,548 | 8/1991 | Sato et al. .................... | 544/352 |
| 5,128,238 | 7/1992 | Nakazyo et al. .............. | 430/378 |

*Primary Examiner*—Mukund J. Shah
*Assistant Examiner*—Ben Schroeder
*Attorney, Agent, or Firm*—Mary E. Bongiorno

[57] ABSTRACT

New compounds, represented by the formulae I and II,

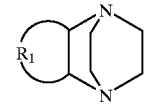

I wherein $R_1$, $R_2$, and $R_3$, are independently $C_3$ or $C_4$, substituted or unsubstituted alkylene groups, are useful for catalyzing the reaction between an organic polyisocyanate and a compound containing a reactive hydrogen to form polyurethanes.

15 Claims, No Drawings

1,4-DIAZABICYCLO[2.2.2]OCTANE COMPOUNDS AND THEIR USE FOR THE PRODUCTION OF POLYURETHANES

BACKGROUND OF THE INVENTION

Polyurethanes are useful in a variety of applications. For example, polyurethane elastomers are used in automotive parts, shoe soles, and other products in which toughness, flexibility, strength, abrasion resistance, and shock-absorbing properties are required. Polyurethanes are also used in coatings and in flexible and rigid foams.

Polyurethanes, in general, are produced by the reaction of a polyisocyanate and a polyol in the presence of a catalyst. The catalyst is typically a low molecular weight tertiary amine such as triethylenediamine.

Polyurethane foams are produced through the reaction of a polyisocyanate with a polyol in the presence of various additives. One class of additives which is particularly effective as blowing agents is the chlorofluorocarbons (CFCs). CFCs vaporize as a result of the reaction exotherm during polymerization and cause the polymerizing mass to form a foam. However, the discovery that CFCs deplete ozone in the stratosphere has resulted in mandates for restricting CFC use. Therefore, more effort has gone into the development of alternatives to CFCs for forming urethane foams and water blowing has emerged as an important alternative. In this method, blowing occurs from carbon dioxide generated by the reaction of water with the polyisocyanate. Foams can be formed by a one-shot method or by formation of a prepolymer and subsequent reaction of the prepolymer with water in the presence of a catalyst to form the foam. Regardless of the method, a balance is needed between reaction of the isocyanate and the polyol (gelling) and the reaction of the isocyanate with water (blowing) in order to produce a polyurethane foam in which the cells are relatively uniform and the foam has specific properties depending on the anticipated application; for example, rigid foams, semi-rigid foams, and flexible foams.

The ability of the catalyst to selectively promote either blowing or gelling is an important consideration in selecting a catalyst for the production of a polyurethane foam with specific properties. If a catalyst promotes the blowing reaction to too high a degree, carbon dioxide will be evolved before sufficient reaction of isocyanate with polyol has occurred. The carbon dioxide will bubble out of the formulation, resulting in collapse of the foam and production of a poor quality foam. At the opposite extreme, if a catalyst promotes the gelling reaction too strongly, a substantial portion of the carbon dioxide will be evolved after a significant degree of polymerization has occurred. Again, a poor quality foam is produced; characterized by high density, broken or poorly defined cells, or other undesirable features. Frequently, a gelling catalyst and a blowing catalyst are used together to achieve the desired balance of gelling and blowing in the foam.

Tertiary amine catalysts are widely used in the production of polyurethanes. The tertiary amine catalysts accelerate both blowing (reaction of water with isocyanate to generate carbon dioxide) and gelling (reaction of polyol with isocyanate) and have been shown to be effective in balancing the blowing and gelling reactions to produce a desirable product.

The most widely used commercial catalysts for producing polyurethanes are triethylenediamine (TEDA), also called 1,4-diazabicyclo[2.2.2]octane, and its derivatives. Representative examples of patents which disclose synthesis of TEDA and substituted TEDA are: U.S. Pat. No. 3,297,701 (Brader et al, 1967), U.S. Pat. No. 3,375,252 (Yamada et al, 1968), U.S. Pat. No. 4,804,758 (Hoelderich et al, 1989), U.S. Pat. No. 5,041,548 (Sato et al, 1991), and U.S. Pat. No. 5,194,613 (King, 1993).

Low molecular weight tertiary amines, such as those described in the above patents, generally have offensive odors and many are highly volatile due to low molecular weight. Release of tertiary amines during polyurethane production may present significant safety and toxicity problems, and release of residual amines from consumer products is generally undesirable.

High molecular weight amine catalysts may possess reduced volatility and odor when compared to known lower molecular weight amines.

BRIEF SUMMARY OF THE INVENTION

The present invention is directed to new compositions which are useful for catalyzing the reaction between an organic polyisocyanate and a compound containing a reactive hydrogen to form polyurethanes. The compositions have been found to be especially effective catalysts for the production of polyurethane foams by way of two reactions—the blowing reaction, in which an organic polyisocyanate reacts with water, and the gelling reaction, in which an organic polyisocyanate reacts with a polyol. The catalyst compositions are represented by the formulae I and II, below:

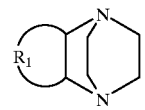

I

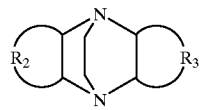

II wherein $R_1$, $R_2$, and $R_3$ are independently $C_3$ to $C_4$ substituted or unsubstituted alkylene groups.

Specific examples of compounds of formulae I and II are represented by formulae III and IV:

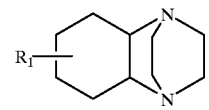

III

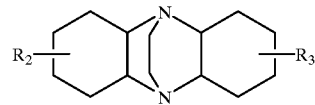

IV wherein $R_1$, $R_2$, and $R_3$ are, independently, hydrogen, an alkyl group, a carboxyl group, an amide, an amine, a hydroxyl group, or a substituted alkyl group in which the substitution is an amide, an amine, a carboxyl group, or a hydroxyl group.

Specific examples of compounds of formula III are shown below.

V

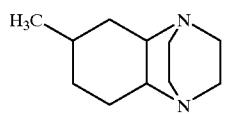

VI

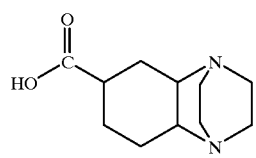

DETAILED DESCRIPTION OF THE INVENTION

The compounds of this invention can be prepared in three steps. The first step is hydrogenation of an unsaturated compound such as those shown below:

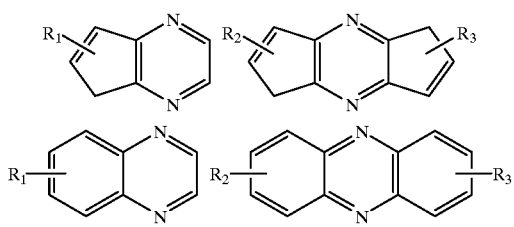

in which $R_1$, $R_2$, and $R_3$ are, independently, hydrogen, an alkyl group, a carboxyl group, an amide, an amine, a hydroxyl group, or a substituted alkyl group in which the substitution is an amide, an amine, a carboxyl group, or a hydroxyl group.

Starting materials, such as those shown above, can be prepared by methods well known in the art. For example, a method for preparing quinoxalines can be found in *J. Org. Chem.*, Vol.45, 1980, pages 2512–2515.

Hydrogenation can be carried out using conventional processes for the hydrogenation of nitrogen containing aromatic compounds. An example of the hydrogenation reaction is presented below in which the starting material is a substituted quinoxaline:

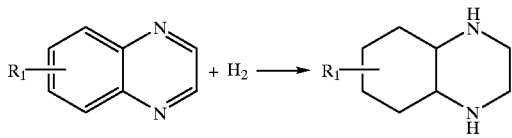

Hydrogenation is typically carried out under liquid phase conditions. Liquid phase conditions are maintained by the use of a solvent such as a lower aliphatic alcohol. Examples of appropriate solvents are ethanol, propanol, isopropanol, n-butanol, 2-butanol, n-pentanol, 2-pentanol, and the like. Isopropanol is a preferred solvent. Optionally, a small amount of other solvents can be used; for example, cyclohexane, tetrahydrofuran, and dioxane. Typically the solvent is used at levels from about 75 to about 200 percent by weight of the aromatic feed. Under some circumstances solvent amounts as high as 1,000 to 2,000 percent by weight based on weight of the aromatic feed may be used.

Generally, the hydrogenation is carried out as a batch process, although it is possible to operate under continuous conditions. Temperatures for such hydrogenation processes range from about 25° C. to 190° C.; preferably 110° C. to 140° C. Hydrogen partial pressures necessary for effecting hydrogenation range from about 1 to 1500 psig (108 to 10,444 kPa); preferably 900 to 1100 psig (6,307 to 7,686 kPa).

The catalyst used in effecting the hydrogenation can be any catalyst known to be effective in the hydrogenation of nitrogen containing aromatic amines. Examples of appropriate catalysts are platinum, palladium, nickel, rhodium and ruthenium and mixtures thereof. Typically the catalysts are carried on a conventional support such as alumina or titania. The preferred catalyst is a rhodium and ruthenium catalyst carried on an alumina support. The catalyst can be used at a concentration of 0.5 to 5% by weight based on the weight of aromatic compound feed.

The progress of hydrogenation can be followed by observing the amount of hydrogen consumed during the reaction. The reaction is terminated when the amount of hydrogen absorbed is generally equal or nearly equal to the amount necessary to effect complete hydrogen of the aromatic starting material. In general, hydrogenation times range from about 30 to 600 minutes. When hydrogenation is complete, the reactor is cooled to ambient temperature (e.g., 25° C.) and depressurized to atmospheric pressure. A mixture of products is typically obtained, ranging from small amounts of unreacted aromatic compound to partially and fully hydrogenated product. The desired product can be separated or partially separated by known crystallization methods.

Ethoxylation is carried out in the second step. An example of this reaction step is presented below:

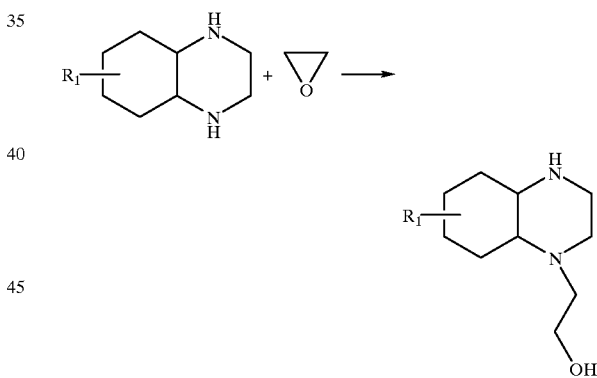

In the ethoxylation step, the hydrogenated compound is charged to a reactor along with a solvent which is compatible with ethylene oxide, such as tetrahydrofuran. The solvent can be used at levels from about 75 to about 200 percent by weight of the hydrogenated feed. The mixture of hydrogenated compound and solvent is heated to 50 to 110° C.; preferably 70 to 90° C. and the pressure increased to 75 to 500 psig (618 to 3549 kPa); preferably 100 to 200 psig (791 to 1480 kPa). Ethylene oxide is then charged to the reactor in a molar ratio of ethylene oxide to saturated compound of about 1 to 2. The mixture is stirred at the elevated temperature and pressure until the reaction is completed. The reactor is then cooled, vented, and purged with nitrogen; and the solvent is vacuum stripped. The reaction products can be used as feed for the ring closure step.

The third step is ring closure. An example of the reaction step is presented below:

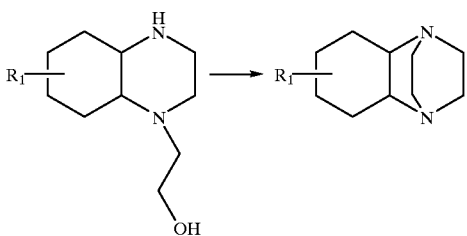

In this step, a catalyst known for use in cyclic dehydration reactions, such as aluminum phosphate, calcium phosphate, or strontium hydrogen phosphate, is loaded into a fixed bed reactor. A continuous process is typically used. The temperature range is about 285 to 420° C., preferably 300 to 370° C., the pressure range is about 0.1 to 1.5 atmospheres (10 to 152 kPa), preferably 0.3 to 1.0 atm (30 to 101 kPa), and the liquid hourly space velocity (LHSV) or organic feedstock per volume catalyst is in the range of 0.05 to 1.5, preferably 0.1 to 0.3. The reaction is carried out in the presence of water and an inert gas such nitrogen, argon, or helium. The molar ratio of inert gas to organic feed is 5 to 50, preferably 20 to 30; and the molar ratio of water to organic feed is 1 to 5; preferably 2 to 3. Products can be separated by known distillation techniques, such as vacuum distillation.

A variety of known methods can be used to prepare the compound represented by formula VI. For example, the methyl group present in 6-methylcyclohexo-1,4-diazabicyclo[2.2.2]octane (formula V) can be oxidized to obtain the corresponding carboxylic acid using a method described in U.S. Pat. No. 2,588,388. This patent discloses a liquid phase catalytic oxidation of alkyl-substituted cyclohexanes to obtain cyclic acids and ketones by means of aldehyde-activated metal catalysts. Alternately, the Amoco commercial process (described in Industrial Organic Chemistry, 2$^{nd}$ ed., by K. Weissermel and H.-J. Arpe, translated by C. R. Lindley, p. 391, VCH Publishers, 1983) which is used for the production of terephthalic acid from p-xylene using, for example, a catalyst combination of cobalt and manganese acetate in 95% acetic acid and promoters such as ammonium bromide and tetrabromoethane, can also be used to synthesize the compound of formula VI.

Variations to the above methods can be employed to optimize the oxidation of 6-methylcyclohexo-1,4-diazabicyclo[2.2.2]octane (formula V) and obtain the desired carboxylic acid compound of formula VI. It is also envisioned that the oxidation of the methyl group can be carried out on the aromatic precursors of 6-methylcyclohexo-1,4-diazabicyclo[2.2.2]-octane. For example, the oxidation can be carried out on 6-methylquinoxaline followed by hydrogenation and ring closure reactions, or on 3,4-touenediamine followed by the condensation, hydrogenation, and ring closure reactions (not necessarily in this order) to ultimately yield the compound of formula VI.

The catalyst compositions of this invention can catalyze (1) the reaction between an isocyanate functionality and an active hydrogen-containing compound, such as, an alcohol, a polyol, an amine or water; especially the gelling reaction of polyols with isocyanate to make polyurethanes and the blowing reaction of water with isocyanate to release carbon dioxide for making foamed polyurethanes, and (2) the trimerization of an isocyanate functionality to form polyisocyanurates.

The polyurethane products are prepared using any suitable organic polyisocyanates well known in the art including, for example, hexamethylene diisocyanate, phenylene diisocyanate, toluene diisocyanate (TDI) and 4, 4'-diphenylmethane diisocyanate (MDI). Especially suitable are the 2, 4- and 2, 6-TDI's individually or together as their commercially available mixtures. Other suitable isocyanates are mixtures of diisocyanates known commercially as "crude MDI", also known as PAPI, which contain about 60% of 4, 4'-diphenylmethane diisocyanate along with other isomeric and analogous higher polyisocyanates. Also suitable are "prepolymers" of these polyisocyanates comprising a partially prereacted mixture of a polyisocyanate and a polyether or polyester polyol.

Illustrative of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, among others, ethylene glycol, propylene glycol, 1, 3-butane diol, 1, 4-butane diol, 1, 6-hexane diol, neopentyl glycol, diethylene glycol, dipropylene glycol, pentaerythritol, glycerol, diglycerol, trimethylol propane and similar low molecular weight polyols.

In the practice of this invention, a single high molecular weight polyether polyol may be used. Also, mixtures of high molecular weight polyether polyols such as mixtures of di- and trifunctional materials and/or different molecular weight or different chemical composition materials may be used.

Useful polyester polyols include those produced by reacting a dicarboxylic acid with an excess of a diol, for example, adipic acid with ethylene glycol or butanediol, or reacting a lactone with an excess of a diol such as caprolactone with propylene glycol.

In addition to the polyether and polyester polyols, the masterbatches, or premix compositions, frequently contain a polymer polyol. Polymer polyols are used in polyurethane foam to increase the foam's resistance to deformation, i.e. to increase the load-bearing properties of the foam. Currently, two different types of polymer polyols are used to achieve load-bearing improvement. The first type, described as a graft polyol, consists of a triol in which vinyl monomers are graft copolymerized. Styrene and acrylonitrile are the usual monomers of choice. The second type, a polyurea modified polyol, is a polyol containing a polyurea dispersion formed by the reaction of a diamine and TDI. Since TDI is used in excess, some of the TDI may react with both the polyol and polyurea. This second type of polymer polyol has a variant called PIPA polyol which is formed by the in-situ polymerization of TDI and alkanolamine in the polyol. Depending on the load-bearing requirements, polymer polyols may comprise 20–80% of the polyol portion of the masterbatch.

Other typical agents found in the polyurethane foam formulations include chain extenders such as ethylene glycol and butanediol; crosslinkers such as diethanolamine, diisopropanolamine, triethanolamine and tripropanolamine; blowing agents such as water, methylene chloride, trichlorofluoromethane, and the like; and cell stabilizers such as silicones.

A catalytically effective amount of the catalyst composition is used in the polyurethane formulation. Suitable amounts of the catalyst composition may range from about 0.01 to 10 parts per 100 hundred parts polyol (phpp). Preferred amounts range from 0.05 to 1.0 phpp.

The catalyst composition may be used in combination with other tertiary amine, organotin and carboxylate urethane catalysts well known in the urethane art. For example, suitable gelling catalysts include but are not limited to trimethylamine, triethylamine, tributyl-amine, trioctylamine, diethyl cyclohexylamine, N-methyl-morpholine, N-ethylmorpholine, N-octadecylmorpholine (N-cocomorpholine), N-methyl-diethanolamine, N, N-dimethylethanolamine, N, N'-bis(2-hydroxypropyl) piperazine, N, N, N', N'-tetramethylethylene-diamine, N, N, N', N'-tetramethyl-1,3-propanediamine, triethylenediamine (1,4-diaza-bicyclo[2.2.2]octane), 1,8-diazabicyclo(5.4.0) undecene-7, 1,4-bis(2-hydroxypropyl)-2-methylpiperazine, N, N-dimethylbenzylamine, N, N-dimethyl-cyclohexylamine, benzyltriethylammonium bromide, bis(N, N-diethylaminoethyl)adipate, N, N-diethylbenzylamine, N-ethylhexamethyleneamine, N-ethylpiperidine, alpha-methyl-benzyldimethylamine, dimethylhexadecylamine, dimethylcetylamine, and the like. Suitable blowing catalysts include but are not limited to bis(dimethylaminoethyl)ether, pentamethyldiethylenetriamine, 2-[N-(dimethylaminoethoxyethyl)-N-methylamino]-ethanol, and the like.

A general polyurethane flexible foam formulation having a 1–3 lb/ft³(16–48 kg/m³) density (e.g., automotive seating) containing a catalyst such as the catalyst composition according to the invention would comprise the following components in parts by weight (pbw):

| Component | Parts by Weight |
| --- | --- |
| Polyol | 20–100 |
| Polymer Polyol | 80–0 |
| Silicone Surfactant | 1–2.5 |
| Blowing Agent (e.g., water) | 2–4.5 |
| Crosslinker | 0.5–2 |
| Catalyst | 0.2–2 |
| Isocyanate Index | 70–115* |

*Isocyanate Index = (mole isocyanate/mole active hydrogen) × 100

The invention will be further clarified by a consideration of the following examples, which are intended to be purely exemplary of the invention.

EXAMPLE 1

SYNTHESIS AND CHARACTERIZATION OF 6-METHYLCYCLOHEXO-1,4-DIAZABICYCLO [2.2.2]OCTANE

This example describes the synthesis of 6-methylcyclohexo-1,4-diazabicyclo[2.2.2]octane (6-MCHDABCO). The synthesis was carried out in three 20 steps. In the first step 6-methylquinoxaline (supplied by Pyrazine Specialties Inc.) was hydrogenated to yield 6-methyidecahydroquinoxaline (6-MDHQ). The structural formula of 6-MDHQ is shown below:

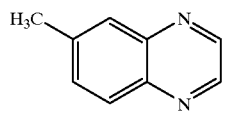

Step 1 was carried out in a batch reactor using a 4.2% RhlO.8% Ru/AI20₃ catalyst obtained from Engelhard. The catalyst (40.5 g) was added to the reactor along with 1178 g of isopropanol for activation prior to hydrogenation of 6-methylquinoxaline. The activation step was carried out for 1.5 hours at 190° C., 1000 psig hydrogen, 500 rpm. After activation, the reactor was cooled and most of the isopropanol removed, before introduction of the feed mixture (600 g of 6-methylquinoxaline plus 1188 g of isopropanol). The reactor was pressurized with hydrogen at 1000 psig and the temperature was increased from 36° C. to 150° C. in about 1 hour, while maintaining hydrogen pressure at approximately 1000 psig. After verifying that there was no more hydrogen consumption, the reactor was cooled and depressurized. GC analysis of the reaction products indicated the following composition:

TABLE 1

| Compound | % GC area |
| --- | --- |
| 6-methylquinoxaline | 3.64 |
| 6-methyldecahydroquinoxaline (isomer #1) | 19.94 |
| 6-methyldecahydroquinoxaline (isomer #2) | 12.07 |
| 6-methyltetrahydroquinoxaline | 64.34 |

Step 2 was ethoxylation of 6-methyidecahydroquinoxaline using ethylene oxide. Partial separation of the 6-methyltetrahydroquinoxaline and 6-methyidecahydroquinoxaline mixture obtained in step 1 was performed using simple crystallization methods. About 212 g of an enriched 6methyidecahydroquinoxaline mixture (64% 6-methyldecahydroquinoxaline plus 29% 6-methyltetrahydroquinoxaline) was charged to a 1000 ml Parr reactor with 200 g of THF (tetrahydrofuran) solvent. The pressure was increased to 100 psig and the reaction mixture was heated to 80° C. Ethylene oxide (150 cc) was then added slowly over 30 minutes. After addition of ethylene oxide, the reaction mixture was stirred for 16 hours at 80° C., 5000 rpm and reactor pressure was in the range of 131–171 psig. When the reaction was completed, the reactor was cooled, vented, and purged with nitrogen, and the solvent was vacuum stripped. Analysis of products using GC, GCIMS and NMR indicated that ethoxylation took place to a great extent.

Step 3 was ring closure of reaction products obtained in step 2. It was carried out in a fixed-bed down-flow stainless steel reactor at atmospheric pressure. About 5 cc (about 5 g) of SrHPO₄ catalyst particles of 18–30 mesh were loaded into the reactor. The reactor was heated to 3400C under a flow of hydrogen. The reaction products obtained from step 2 were introduced to the reactor with a syringe pump at 0.65 cc/hr. Water was co-fed to the reactor using an Isco pump at 2.85 cc/hr. Hydrogen was also co-fed at a flow rate of 50 cc/min. Reaction products were collected and analyzed using GC. A typical reaction product composition is indicated in Table 2.

TABLE 2

| Compound | % GC area |
| --- | --- |
| Piperazine | 2.3 |
| Triethylenediamine | 6.3 |
| Quinoxaline | 1.8 |
| 6-Methylquinoxaline | 1.4 |
| 6-Methyldecahydroquinoxaline | 4.4 |
| 6-MBDABCO[a] | 4.9 |
| 6-MCHDABCO[b] (isomers) | 57.6 |
| Unknowns | 21.3 |

[a]6-methylbenzo-1,4-diazabicyclo[2.2.2]octane
[b]6-methylcyclohexo-1,4-diazabicyclo[2.2.2]octane (four isomers were identified using GC/MS); formula V A spinning band distillation apparatus was used to isolate of 6-methylcyclohexodiazabicyclo-12.2.2]octane (6-MCHDABCO). Nine separate cuts were collected from 60° C. to 120° C. at 11 torr vacuum and 50:1 reflux ratio. Samples of 6-MCHDABCO with purity of up to 99+% were obtained.

Identification of 6-MCHDABCO was carried out initially using chemical ionization mass spectroscopy. $ND_3$ was used as the reagent gas to distinguish, via the presence of exchangeable protons, among primary, secondary and tertiary amines. Further detailed GC/IMS analysis of the reaction product samples revealed the presence of four isomers of 6-MCHDABCO.

Some physical properties of 6-MCHDABCO are listed in Table 3. These were obtained with a 99.7% pure 6-MCHDABCO sample. Presence of small impurities or relatively different concentrations of 6-MCHDABCO isomers may have an impact in these physical properties.

TABLE 3

| Formula | $C_{11}H_{20}N_2$ |
|---|---|
| Molecular Weight | 180 |
| Appearance at Ambient Temperature | Light Yellow Liquid |
| Density, 25° C. | 1.03 g/ml |
| Boiling Point, ° C. | 281 |
| Freezing Point, ° C. | −15 |
| Viscosity, centipoise | 13.8 |

EXAMPLE 2

POLYURETHANE FOAM PRODUCTION USING 6-MCHDABCO AS A CATALYST

This example describes the application of 6-MCHDABCO (Example 1) as a catalyst for the production of polyurethane flexible foam.

A polyurethane foam was prepared using the following formulation:

| Component | Parts by Weight |
|---|---|
| E-648 (ethylene oxide tipped polyether polyol marketed by Lyondell) | 60 |
| E-519 (styrene-acrylonitrile copolymer filled polyether polyol marketed by Lyondell) | 40 |
| DABCO ® DC-5043 (silicone surfactant marketed by Air Products and Chemicals, Inc. | 1.5 |
| Diethanolamine | 1.49 |
| Water | 3.5 |
| TDI 80 (mixture of 80 wt % 2,4-TDI and 20 wt % 2,6-TDI) | 105 Index |

The catalyst was added to 202 g of the premix in a 32 oz. (951 ml) paper cup and the formulation was mixed for 20 seconds at 12000 RPM using an overhead stirrer fitted with a 2 in. (5.1 cm) diameter stirring paddle. Sufficient TDI 80 was added to make a 105 index foam [index=(mole NCO1-mole active hydrogen)×100] and the formulation was mixed well for 5 seconds using the same overhead stirrer. The 32 oz. cup was dropped through a hole in the bottom of a 128 oz. (3804 ml) paper cup placed on a stand. The hole was sized to catch the lip of the 32 oz. cup. The total volume of the foam container was 160 oz. (4755 ml). Foams approximated this volume at the end of the foam forming process.

Times (in seconds) cited were from mixing of the polyol with isocyanate. Top of Cup 1 (TOC 1) represents the time required for the foam formulation to fill a 32 oz. cup and is an indication of reaction initiation. Top of Cup 2 (TOC 2) represents the time required for the foam formulation to fill a 1 gal bucket in addition to the 32 oz. cup mentioned above and is an indication of reaction progression. String Gel and Full Rise are further measures of reaction progression and provide some indication of extent of cure. Catalyst use levels were chosen to match string gel times. Results are presented in Table 4.

TABLE 4

| Catalyst | pphp | TOC 1 | TOC 2 | String Gel | Full Rise |
|---|---|---|---|---|---|
| Dabco 33LV[a]/ Dabco BL-11[b] | 0.25/0.11 | 13.6 | 40.1 | 68.6 | 111.5 |
| Ex. 1 catalyst/ Dabco BL-11 | 0.16/0.11 | 13.8 | 39.7 | 66.7 | 117.9 |

[a]gelling catalyst; 33 wt % triethylenediamine in dipropylene glycol
[b]blowing catalyst; 70 wt % bis(N,N-dimethylaminoethyl)ether in dipropylene glycol.

These data show that 6-MCHDABCO (prepared in Example 1) is an excellent gelling catalyst.

What is claimed is:

1. A compound having a chemical formula I or II,

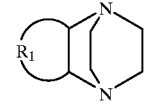

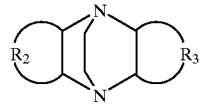

wherein each of $R_1$, $R_2$, and $R_3$ is independently a $C_3$ or $C_4$ substituted or unsubstituted alkylene group[s], provided at least one of $R_2$ and $R_3$ is substituted when $R_2$ and $R_3$ are both $C_4$ alkylene.

2. The compound of claim 1 wherein the chemical formula is III or IV,

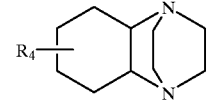

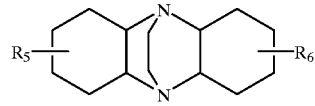

and each of $R_4$, $R_5$, and $R_6$ is independently selected from the group consisting of hydrogen, an alkyl group, a carboxyl group, an amide, an amine, a hydroxyl group, or a substituted alkyl group in which the substitution is an amide, an amine, a carboxyl group, or a hydroxyl group, provided at least one of $R_5$ and $R_6$ is other than hydrogen.

3. The compound of claim 2 wherein the chemical formula is III.

4. The compound of claim 2 having the chemical formula

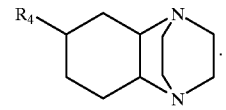

5. The compound of claim 4 wherein $R_4$ is methyl or carboxylic acid.

6. A method for preparing a polyurethane comprising reacting an organic polyisocyanate with a compound having a reactive hydrogen in the presence of a catalytically effective amount of a compound having chemical formula I or II:

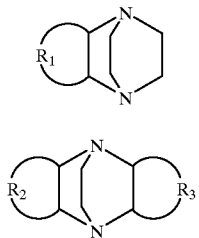

I

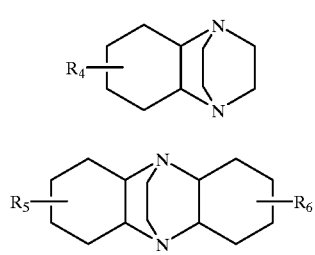

II wherein each of $R_1$, $R_2$ and $R_3$ is independently a $C_3$ or $C_4$ substituted or unsubstituted alkylene group.

7. The method of claim 6 wherein the chemical formula is III or IV,

III

IV

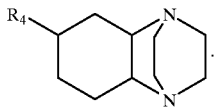

and each of $R_4$, $R_5$, and $R_6$ is independently selected from the group consisting of hydrogen, an alkyl group, a carboxyl group, an amide, an amine, a hydroxyl group, or a substituted alkyl group in which the substitution is an amide, an amine, a carboxyl group, or a hydroxyl group.

8. The method of claim 7 wherein the chemical formula is III.

9. The method of claim 8 wherein the compound has the chemical formula:

10. The method of claim 9 wherein $R_4$ is methyl or carboxylic acid.

11. A method for preparing a polyurethane foam comprising reacting an organic polyisocyanate with a polyol in the presence of water and a catalyst composition comprising a compound having chemical formula I or II:

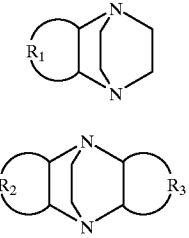

I

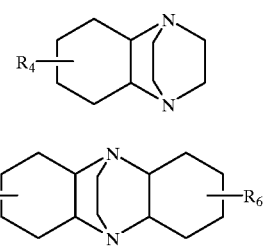

II wherein each of $R_1$, $R_2$, and $R_3$ is independently a $C_3$ or $C_4$ substituted or unsubstituted alkylene group.

12. The method of claim 11 wherein the chemical formula is III or IV, below,

III

IV

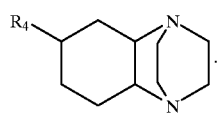

and each of $R_4$, $R_5$, and $R_6$ is independently selected from the group of hydrogen, an alkyl group, a carboxyl group, an amide, an amine, a hydroxyl substituted alkyl group in which the substitution is an amide, an amine, a oup, or a hydroxyl group.

13. The method of claim 12 wherein the chemical formula is III.

14. The method of claim 13 wherein the compound has the chemical

15. The method of claim 14 wherein $R_4$ is methyl or carboxylic acid.

* * * * *

UNITED STATES PATENT AND TRADEMARK OFFICE
CERTIFICATE OF CORRECTION

PATENT NO : 6,147,185

DATED : November 14, 2000

INVENTOR(S) : J. G. Santiesteban, et al.

It is certified that error appears in the above-identified patent and that said Letters Patent are hereby corrected as shown below:

Column 12, line 36
    Delete "oup" and substitute therefor -- carboxyl group --

Signed and Sealed this

Eighth Day of May, 2001

*Attest:*

NICHOLAS P. GODICI

*Attesting Officer*     *Acting Director of the United States Patent and Trademark Office*